(12) United States Patent
Escher et al.

(10) Patent No.: US 6,821,728 B1
(45) Date of Patent: Nov. 23, 2004

(54) SCREENING SYSTEM

(75) Inventors: Dominik Escher, Zürich (CH); Alcide Barberis, Zürich (CH)

(73) Assignee: ESBATech AG, Zurich (CH)

(*) Notice: Subject to any disclaimer, the term of this patent is extended or adjusted under 35 U.S.C. 154(b) by 0 days.

(21) Appl. No.: 09/720,106

(22) PCT Filed: Jun. 22, 1999

(86) PCT No.: PCT/IB99/01168
§ 371 (c)(1),
(2), (4) Date: Mar. 9, 2001

(87) PCT Pub. No.: WO99/67375
PCT Pub. Date: Dec. 29, 1999

(30) Foreign Application Priority Data

Jun. 22, 1998 (EP) ............................................ 98111428

(51) Int. Cl.⁷ ................................................. C12Q 1/68
(52) U.S. Cl. ......................................................... 435/6
(58) Field of Search ............................................. 435/6

(56) References Cited

U.S. PATENT DOCUMENTS 4,937,193 A    6/1990   Hinchliffe et al.

FOREIGN PATENT DOCUMENTS

| WO | WO 95/19367 | 7/1995 |
|----|-------------|--------|
| WO | WO 95/26400 | 10/1995 |
| WO | WO 95/34646 | 12/1995 |
| WO | WO 96/14334 | 5/1996 |
| WO | WO 96/37618 | 11/1996 |
| WO | WO 96/40721 | 12/1996 |
| WO | WO 97/23609 | 7/1997 |
| WO | WO 98/13502 | 4/1998 |

*Primary Examiner*—Terry McKelvey
(74) *Attorney, Agent, or Firm*—Marshall, Gerstein & Borun LLP

(57) ABSTRACT

The present invention concerns a screening system for screening effector peptides that can act as agonists or antagonists, as well as means to produce such a screening system, in particular a specific DNA library encoding peptides. In order to perform the screening, host cells comprising a selection system are transformed with the DNA library and the thus obtained screening system is then cultivated under conditions selectively allowing survival of cells with desired interaction.

14 Claims, 10 Drawing Sheets

Expression of mutant p53 and millions of different peptides in vivo

Binding of the peptide allows mutant p53 to restore DNA binding activity

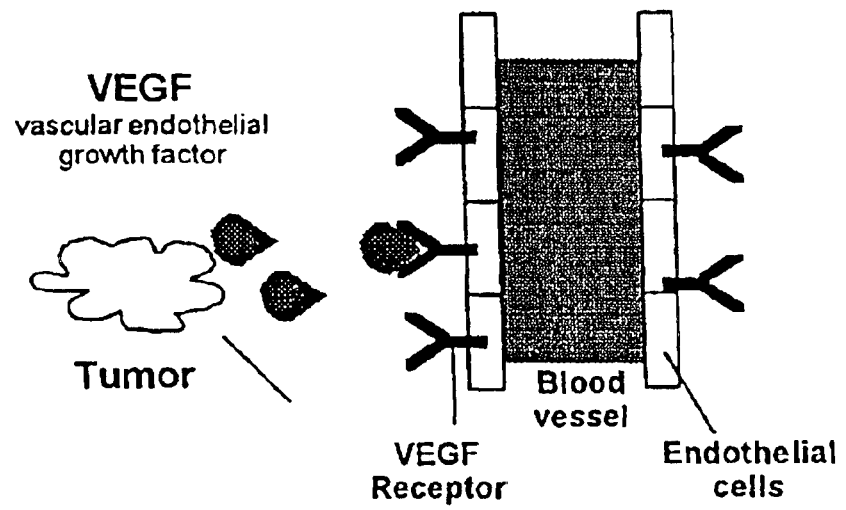
Figure 5
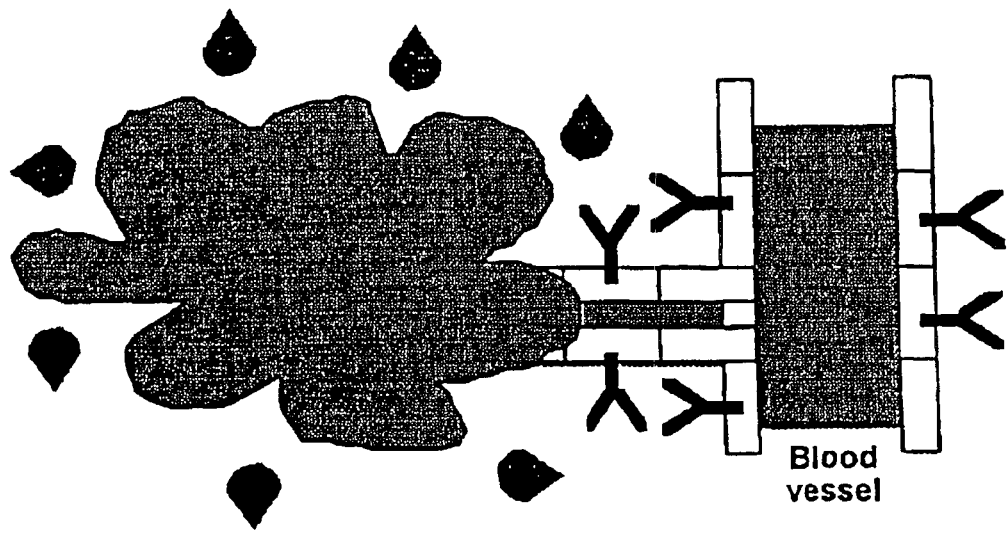
Figur 6

SCREENING SYSTEM

CROSS REFERENCES TO RELATED APPLICATIONS

This application claims the priority of European patent application no. 98111428.3, filed Jun. 22, 1998, the disclosure of which is incorporated herein by reference in its entirety.

TECHNICAL FIELD

The present invention concerns a screening system, to identify lead compounds. Said screening system is especially suitable for the screening of small molecules, whereby peptides are the much preferred small molecules.

BACKGROUND ART

Screening compounds in order to find molecules for further drug development, is one of the crucial steps in such drug development. Up to now, product screening is performed in vitro, e.g. by so called high-throughput screening systems or by phage display. Phage display systems can identify proteins or peptides which are expressed on the surface of a bacteriophage particle (see R. Cortese et al., *Selection of biologically active peptides by phage display of random peptide libraries*, Current Opinion in Biotechnology 1996, 7, 616–621, 1996). Only in the case of a successful interaction between the two proteins, the bacteriophage can infect the bacterial *E. coli* host. This event becomes visible since this successful bacteriophage will spread and form plaques which consist of lysed *E. coli* cells. High throughput screening systems suitable for the screening of small molecules are e.g. described in WO 9710253 by Merck & Co. Inc. Such systems are generally applied for the screening of e.g. plant extracts, etc. in vitro.

These screening systems of the state of the art are very laborious and time-consuming.

The disadvantage of these screening systems of the state of the art is that they are far away from natural conditions and very slow. In particular, no post-translational modifications of proteins occur in the phage display system. Additionally, the interactions of the phage system occur in vitro, whereas the interesting protein—protein interactions in mammals, including man, actually occur in the cell, many of them in the nucleus.

It is also known to study protein—protein interactions in vivo by using two hybrid proteins. The protein of interest is fused to a DNA binding domain, e.g. a GAL4 DNA binding domain, whereas a library of potential interaction candidates is fused to a transcription activation domain, e.g. a GAL4 transcription activation domain. Only in the case of successful interaction between the protein of interest and a real interacting candidate, the transcriptional activation domain is brought to the reporter gene (lacZ), which leads to a blue colouring of this cell (see Fields and Song, *A novel genetic system to detect protein—protein interactions*, Nature 340, 245, 1989). Such systems are additionally described in reviews and patent literature (see e.g. S. Fields and R. Sternglanz, The Two-hybrid System: An Essay for Protein-protein Interactions, Reviews, TIG August 1994, Vol. 10, No. 8, p. 286–292, and *The Matchmaker Two-hybrid System*, published by Clontech, as well as U.S. Pat. Nos. 5,283,173 and 5,468,614 both assigned to the Research Foundation of the State University of New York). A further two-hybrid system, which is a modification of the classical one, and which—due to the modification—is dependent on post-translational modifications of one of the proteins, is described in U.S. Pat. No. 5,637,463. Such two-hybrid systems are disclosed to have three major applications: Testing known proteins for interaction, defining domains or amino acids critical for an interaction, and screening libraries for proteins that bind some target protein. It is also known to modify the existing classical two-hybrid screening. Instead of fusing a library of cellular proteins to an activation domain, peptide libraries are fused to the GAL4 activation domain (see WO97/41255, WO95/34646, WO92/05286, FR 2720068). It is also known to fuse a peptide library to a DNA binding domain (see U.S. Pat. No. 5,498,530). The selection principle is identical to the classical two-hybrid (see Young, Wo and Fields, *Protein—peptide interactions analysed with the yeast two-hybrid system*, Nucl. Acids Res. 23, 1152, 1995).

Another DNA-binding domain and activation domains e.g. disclosed in connection with screening for peptides which interact with the cyclin dependent kinase II. Here, the Cdk2 was fused to a LexA DNA binding domain, and the peptide library was cloned into the active loop of the *E. coli* thioredoxin, which was also fused to an activation domain (see Colas, Cohen, Jessen, Grishina, McCoy & Brent, *Genetic selection of peptide aptamers that recognise and inhibit cyclin-dependent kinase II*, Nature, 30, 554, 1996 and WO 94/10300). Information about other reporter genes can be found in Vidal, Brachmann, Fatai, Harlow and Böcke, Reversed two-hybrid to detect dissociation of protein—protein and DNA protein interactions, Proc. Natl. Acad. Sci. USA 93, 10315, 1996, and Vidal, Brown, Chen, Böcke and Harlow, *Genetic characterisation of a mammalian protein—protein interaction domain by using a yeast reverse two-hybrid system*, Proc. Natl. Acad. Sci. USA 93, 10321, 1996.

Other two-hybrid systems were described by A. Aronheim et al., *Isolation of an AP-1repressor by a novel method for detecting protein—protein interactions*, Mol. Cell. Biol. 17, 3094–3102, 1997; and by I. Stagljar et al., *A genetic system based on split-ubiquitin for the analysis of interactions between membrane proteins in vivo*, Proc. Natl. Acad. Sci. USA 95, 5187–5192, 1998. In the Aronheim report a two-hybrid system based on the mammalian GDP-GTP exchange factor (GEF)hSoS is described.

Also known are so-called three-hybrid systems to detect RNA-protein interactions (see e.g. D. J. SenGupta et al., *A three-hybrid system to detect RNA-protein interactions in vivo*, Proc. Acad. Natl. Sci. USA 93, 8496–8501, 1996), or mediating proteins (WO97/24457).

The two-hybrid method, as it is described in the above mentioned literature, thus allows to study molecular interactions that might be the causes of diseases. However, it does not show how to use such systems in the search for active substances and the development of novel drugs.

It is also already known to use the two-hybrid technology to find exogenous small molecules, which inhibit protein—protein interaction (see WO97/41255, U.S. Pat. No. 5,569,588, WO92/05286). Hybrid proteins, of which the interaction should be disrupted, can also be expressed as fusions to a DNA binding domain (LexA) and an activation domain (B42). The small molecule can be covalently linked to a polymer bead, which is photoreleasable from the small molecule (see Huang & Schreiber, *A yeast genetic system for selecting small molecule inhibitors of protein—protein interaction in nano droplets*, Proc. Natl. Acad. Sci. USA 94, 1336, 1997).

This technology is not suitable for a screening of interacting peptides, since it is laborious in view of the production of peptides, and the analysis of the possibly interacting peptides.

Attempts to screen HIV-1 Rev protein inhibitors have already been made (U.S. Pat. No. 5,691,137 to Brandeis University, Waltham, Mass.). In said attempts the re-porter gene used was CUP 1 modified by insertion of an intron sequence, and a HIV-1 Rev response element 3' of the CUP 1 open reading frame. Upon interaction of Rev with its response element, the splicing of the pre-mRNA is inhibited leading to a inactive protein.

DISCLOSURE OF THE INVENTION

Hence, it is a general object of the invention to provide a much faster screening system allowing the trial of many different effector peptides with agonist or antagonist effect in parallel, whereby the time and costs of the first step in drug development can be dramatically reduced.

This object is achieved by providing a screening system for agonists or antagonists comprising a eukaryotic host cell stably transformed with a selection system enabling the survival of the cells in the case of desired interaction between at least one target protein and an effector peptide, and a peptide expressing system, whereby said selection system comprises
at least one monitoring gene enabling the detection of said host cell upon transcription of said monitoring gene, said at least one monitoring gene being directly or indirectly under the control of a specific activation system and,
at least one DNA sequence coding for at least one target molecule, said one or more target molecule(s) being selected from the group comprising RNA sequences or proteins, said one or more target molecule(s) being responsible in their natural environment for the induction of the production and/or activity of an undesired protein or the omission of the production and/or activation of a desired protein, said at least one DNA sequence coding for said at least one target molecule being under the control of an host cell specific active promoter, preferably a host cell specific promoter,
whereby said specific activation system is selectively modulated (i.e. activated or inactivated) in the presence of specific interaction(s) between at least one of said target protein(s) and an effector peptide,
whereby said specific activation system upon modulation directly or indirectly modulates the transcription of at least one monitoring gene enabling the survival of said host cell, and
whereby said effector peptide expressing system comprises a peptide encoding nucleic acid sequence under the control of an active promoter, preferably a host cell specific active promoter.

In a preferred embodiment, said at least one monitoring gene is a nucleic acid sequence encoding at least one monitoring protein enabling the detection of said host cell upon expression of said at least one monitoring protein, said at least one nucleic acid encoding said at least one monitoring protein being under the control of said specific activation system, and whereby said specific activation system upon modulation modulates the expression of at least one monitoring protein enabling the survival of said host cell, Other objects of the present invention are a screening method, a method for the production of a screening system, a DNA library as peptide source, and a method to produce such library.

BRIEF DESCRIPTION OF THE DRAWINGS

The Invention will be better understood and objects other than those set forth above will become apparent when consideration is given to the following detailed description thereof. Such description makes reference to the annexed drawings, wherein:

FIG. 5 represents the action of vascular endothelial growth factor in the presence of a tumor on the level of induction of angiogenesis.

FIG. 6 represents a later state of the system represented in FIG. 5, namely tumor growth and metastasis formation due to angiogenesis.

MODES FOR CARRYING OUT THE INVENTION

Figure 1:
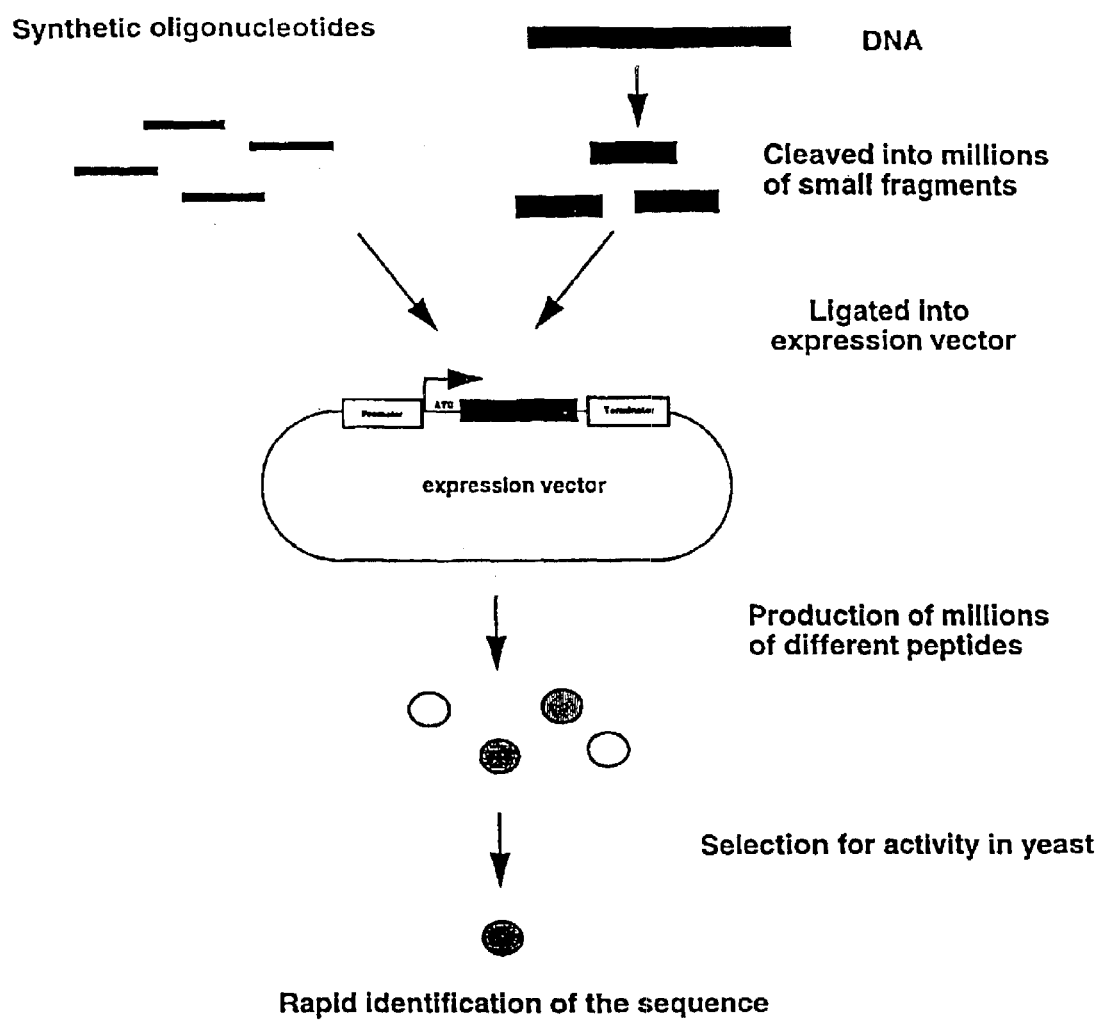
FIG. 1 is a representation of the generation of a DNA library suitable for peptide expression in yeast.

As mentioned above, a general object of the present invention is to provide a much faster screening system for agonists or antagonists allowing the trial of many different effector peptides in parallel, whereby the time and costs of the first step in drug development can be dramatically reduced. This object is achieved by providing a screening system for agonists or antagonists comprising a eukaryotic host cell stably transformed with a selection system enabling the survival of the cells in the case of desired interaction between at least one target protein and an effector peptide, and a peptide expressing system, whereby said selection system comprises
at least one monitoring gene enabling the detection of said host cell upon transcription of said monitoring gene, said at least one monitoring gene being directly or indirectly under the control of a specific activation system and,
at least one DNA sequence coding for at least one target molecule, said one or more target molecule(s) being selected from the group comprising RNA sequences or proteins, said one or more target molecule(s) being responsible in their natural environment for the induction of the production and/or the activity of an undesired protein or the omission of the production and/or the activation of a desired protein, said at least one DNA sequence coding for said at least one target molecule being under the control of an host cell specific active promoter, preferably a host cell specific promoter,
whereby said specific activation system is selectively modulated (i.e. activated or inactivated) in the presence of specific interaction(s) between at least one of said target protein(s) and an effector peptide,
whereby said specific activation system upon modulation directly or indirectly modulates the transcription of at least one monitoring gene enabling the survival of said host cell, and whereby said effector peptide expressing system comprises a peptide encoding nucleic acid sequence under the control of an active promoter, preferably a host cell specific active promoter.

In a preferred embodiment, said at least one monitoring gene is a nucleic acid sequence encoding at least one monitoring protein enabling the detection of said host cell upon expression of said at least one monitoring protein, said at least one nucleic acid encoding said at least one monitoring protein being under the control of said specific activation system, and whereby said specific activation system upon modulation modulates the expression of at least one monitoring protein enabling the survival of said host cell.

Monitoring genes suitable for the present invention are e.g. genes encoding defined proteins the activity of which can be directly monitored.

The modulation of the transcription means that transcription can either be activated or inactivated, and direct modulation, refer so the direct effect on the transcription of the monitoring gene whereas indirect modulation refers to a stimulation of cellular signals resulting in cell growth due to activation of cell-cycle regulatory genes.

Inventive screening systems allow the screening of effector peptides with agonist as well as antagonist activity.

In order to prepare a screening system according to the present invention, information about relevant interactions, influenced by the effector peptide, and preferably the causes, or at least a part of said causes, of the respective disease to be treated by the effector peptide itself, or an active substance derived from or developed on the bases of such effector peptide have to be known.

On the basis of such knowledge, a selection principle according to the present invention, applicable according to the method of the present invention, is produced.

Different causes for diseases exist, such as expression of a defective protein no longer able to activate the expression of another essential protein, expression of proteins interacting with each other or with nucleic acid(s), whereby said interaction(s) lead(s) to an undesired response in the cell, expression of a defective protein such, that a necessary protein—protein or protein-nucleic acid interaction is impossible, expression of a protein activating an undesired cell response.

The screening system of the present invention allows to find peptides interacting with at least one of such proteins or nucleic acids in a manner enabling a "normal" cell function.

The screening system of the present invention is suitable for the identification of agonists and/or antagonists modulating molecular interactions and molecular conformation, such as e.g. protein—protein interactions, protein-RNA interactions, protein-DNA interactions. In particular, agonists and antagonists to protein—protein and protein-DNA interactions are easily studied. The screening system of course is also suitable for optimizing specific peptides, e.g. already known peptides, in that a library encoding modifications is used. Such a library can be produced by mutating the peptide encoding DNA sequence.

A preferred eukaryotic host cell is a yeast cell. Yeast cells are known to perform similar co-translational and post-translational modifications as mammalian cells. Additionally, yeast cells have the advantage of the ease of transformation, the convenience of retrieving plasmids and the availability of nutritional markers and well-characterised monitoring protein expressing selector/reporter genes for direct selection. Furthermore, endogenous yeast proteins are less likely to bind a mammalian protein, the binding of which would reduce the reliability of the screening system. However, the system of the present invention is not limited to yeast cells. In particular, where specifically folded, glycosilated or otherwise modified proteins or peptides might be at issue, other mammalian cells can be used.

While also other small molecules can be screened by host cells comprising at least one nucleic acid sequence encoding at least one monitoring protein and at least one nucleic acid sequence encoding at least one target protein as described above, the screening system of the present invention is in particular suitable in cases where the interacting molecules, i.e. the effector molecules, are peptides. In this case it has been found that a very efficient screening is obtained, if peptide encoding DNA sequences are introduced into the cells. Such introduction is best performed by generating a DNA library. Such DNA library can e.g. be obtained by fragmentation of genomic DNA or cDNA by digestion or, preferably, by sonication and digestion with several restriction enzymes, or by synthesis of random oligo-nucleotides or, in particular in the case where known peptide agonists or antagonists shall be improved, by mutation of respective peptide encoding DNA. The respectively obtained DNA fragments are then introduced into plasmid vectors, so that they are under the control of a host cell specific active promoter (see FIG. 1). Further to the expression of the peptides as such, they can be expressed fused to defined proteins. Such defined proteins preferably have no own activity in the screening system. Such methods of processing DNA fragments are known from general DNA library technology. Such a DNA library with sequences encoding peptides (peptide library) is also part of the present invention. Preferred peptide libraries are those, wherein each peptide encoding sequence is incorporated in a separate plasmid vector, said plasmid vector enabling transformation of the respective host cell and episomal expression of the peptide.

The host cells, comprising a selection system are then brought into contact with such an inventive DNA library, preferably in a manner that one peptide encoding sequence, e.g. one peptide encoding sequence comprising plasmid, is introduced per cell.

In the case of host cell survival, showing the presence of a desired interaction, the peptide encoding DNA comprised in the surviving cells can be isolated, analysed and multiplied to get information on the interacting peptide. Additionally, such surviving yeast cells, or the cloned DNA in other production cells, can be used to produce the interacting peptide, i.e. the effector peptide.

The advantage of the inventive screening method thus is, that billions of different small peptides can easily be generated and analysed, and that the method additionally provides a system allowing inexhaustible production of the peptide of interest, or all means necessary to prepare such a system, respectively.

Another important part of the present invention is the selection system, with which the host cells are transformed. Such selection systems are now further described for each of the above mentioned types of defects or in view of the desired molecule to be found, respectively.

Searching for agonists to one defective protein

Many diseases are due to the fact that an essential protein is not expressed because of a defect in a transcription activating protein. The screening system of the present invention is suitable to search for small molecules able to "restore" the activating abilities of such defective proteins. For such screenings, the monitoring system comprises a transcription activating sequence that is activated upon contact with a "restored" protein and is responsible for the expression of a protein essential for the survival of the cell under the respective selection conditions.

A host cell for this specific application is produced in that it is transformed with a DNA sequence, encoding a defective protein to be restored and additionally with a selector/reporter gene enabling the survival of the cell in a specific selection medium if expressed, said selector/reporter gene being under the control of a transcription activating sequence activated by the "restored" protein. Such a stably transformed host cell can then be brought into contact with a DNA library encoding a plurality of peptides.

Figure 2:
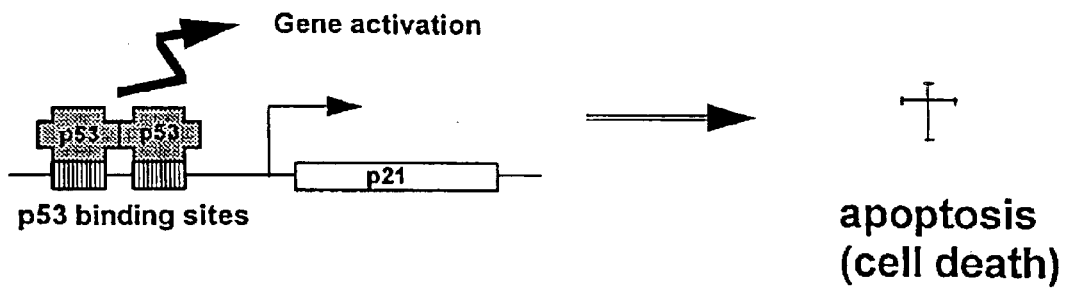
FIG. 2 shows the action of p53.
Figure 3:
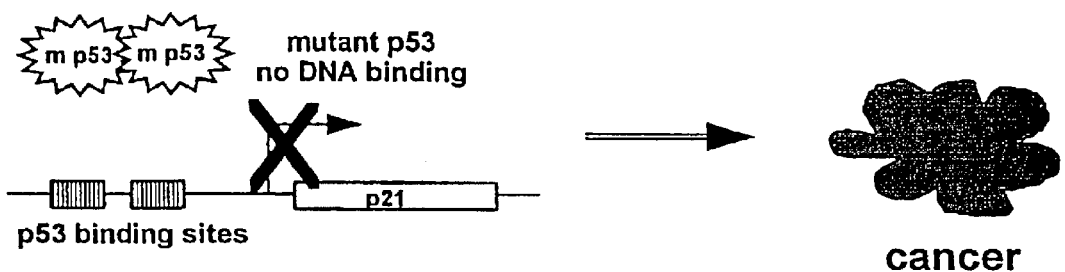
FIG. 3 shows the effect of mutant p53.

One of such transcription activating proteins is the p53 tetramer. p53 is a tumor suppressor gene which encodes a sequence-specific DNA-binding transcription factor. Through its ability to bind DNA, the p53 protein is responsible for the activation of specific genes required for cell cycle arrest or apoptosis, i.e. the "suicide" of a cell which has been damaged by e.g. cancerogenic substances (see FIG. 2). In many tumor cells, p53 has been mutated such that it no longer binds DNA, and it is therefore unable to activate the apoptotic genes. The loss of p53 activity and the consequent lack of apoptosis leads to uncontrolled growth of cancer cells and therefore to tumor development (see FIG. 3). Mutations in p53 that abolish DNA binding are thought to change the shape of this protein so that it can no longer perform its natural function. It has been shown that molecules such as antibodies and synthetic peptides that can touch mutated p53 at specific sites, can reshape this protein so that it regains its natural conformation and therefore its DNA binding function (see Selivanova et al. *Restauration of the Growth Suppression Function* . . . , Nature Medicine, Vol. 3 No. 6, 632 ff., 1997).

In such cases it is therefore very desirable to have a method to screen a lot of peptides in order to find suitably interacting peptides.

Figure 4:
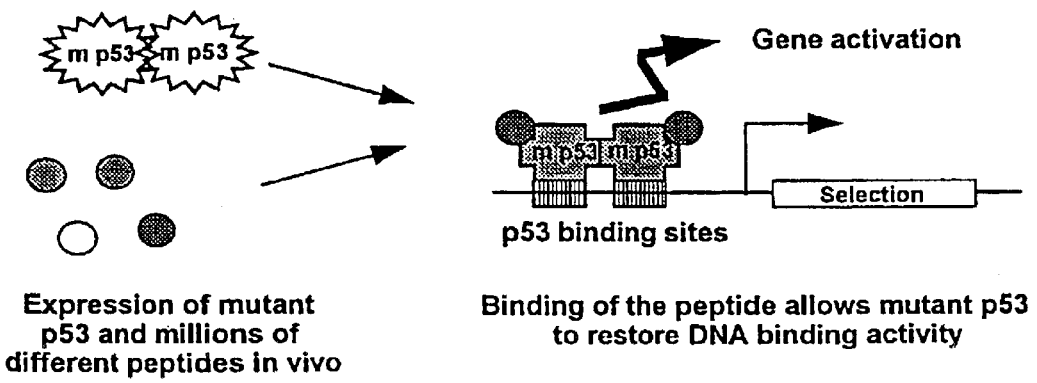
FIG. 4 shows the essential features of a screening system of the present invention for the screening of a mutant p53 agonist.

In the case of the mutant p53 protein the inventive selection system works as follows;

p53 can be expressed in yeast cells where it can activate genes in a sequence-specific manner. Similarly to what happens in human cells, the mutated forms of p53 that are no longer capable of binding DNA cannot activate genes in yeast. This property of yeast cells can be exploited in the inventive screening system. The natural, non-mutated form of p53 can activate the expression of an artificial gene in yeast which is essential for cell growth. As a consequence of this natural p53 activity, and only in this case, yeast colonies will appear on an appropriate terrain. On the contrary, the mutant form of p53 which has lost the ability to bind DNA, cannot activate the expression of the artificial gene in yeast. As a consequence of this lack of activity, yeast cells containing the mutant p53 will not be able to grow and to form colonies on the appropriate terrain. In these cells, a small peptide with the ability to interact with the mutant p53, and to restore its natural activity will cause activation of the artificial gene by the mutant p53 (see FIG. 4). Expression of the artificial, essential gene will allow growth of the yeast cells and, therefore, formation of colonies.

In order to easily get information on the respective peptide being able to restore the p53 action, the suitable host cells are brought into contact with a peptide library. Briefly put, the respective procedure is as follows. Random, short DNA sequences, which are generated by fragmentation of natural DNA molecules or by synthesis are spliced into so-called yeast expression vectors (see FIG. 1). This procedure can generate billions of different DNA sequences (DNA fragments) carried by billions of expression vectors (see FIG. 1). These DNA vectors are then introduced into billions of yeast cells, such that in general each cell receives one individual DNA fragment. Inside yeast cells, the different random DNA sequences (DNA fragments) are expressed as part of genes to produce an equivalent high number of random peptides. Due to the specific monitoring systems, only those yeast cells that produce peptides capable of reactivating the mutant p53, which in turn activates the artificial gene, can grow to form colonies.

Growing colonies are then further cultivated, and the expression vector molecule carrying the DNA sequence that generated the active peptide can be extracted from the yeast cells for characterisation. DNA molecules can be quickly characterised by sequence analysis, and the amino acid sequence of the active peptide can be easily deduced. Because these isolated DNA molecules are clones, they can be multiplied indefinitely and they directly represent an inexhaustible source of the active peptides, the effector peptides.

As it is shown above with reference to p53, the screening system of the present invention is easily applicable in such cases where the binding site and the defective protein are known. Knowing the defective protein of course allows to use a sequence encoding such defective protein which is adapted to the specific host cell.

Screening for antagonists to suppress protein—protein interaction

It is also known that some responses in cells are activated by protein—protein interactions. If natural regulation of such interaction is lost or modified, this could, for example, result in undue cellular proliferation that might lead to tumor formation, or faster tumor growth, or metastasis formation. It is thus desirable to find antagonists suitable to block such interactions. Such antagonists can also be small peptides, advantageously detectable with the inventive screening system.

Figure 7:
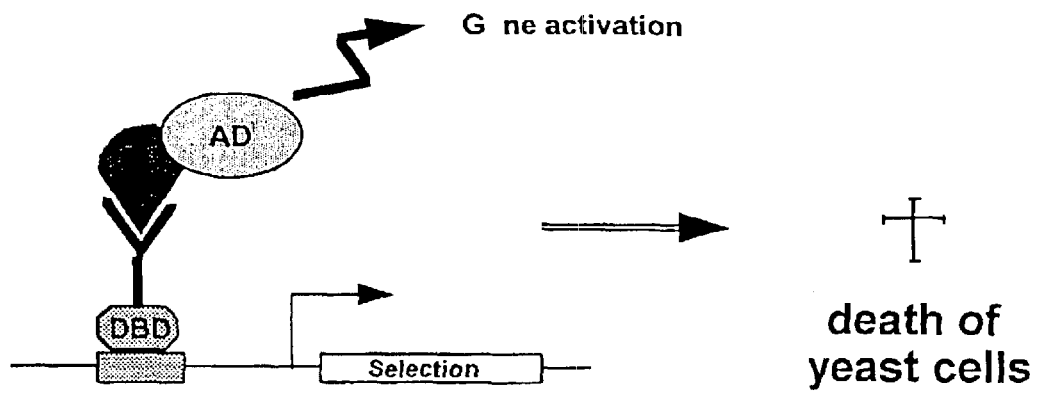
FIG. 7 represents the situation during the screening of a host cell in the absence of an antagonist.
Figure 8:
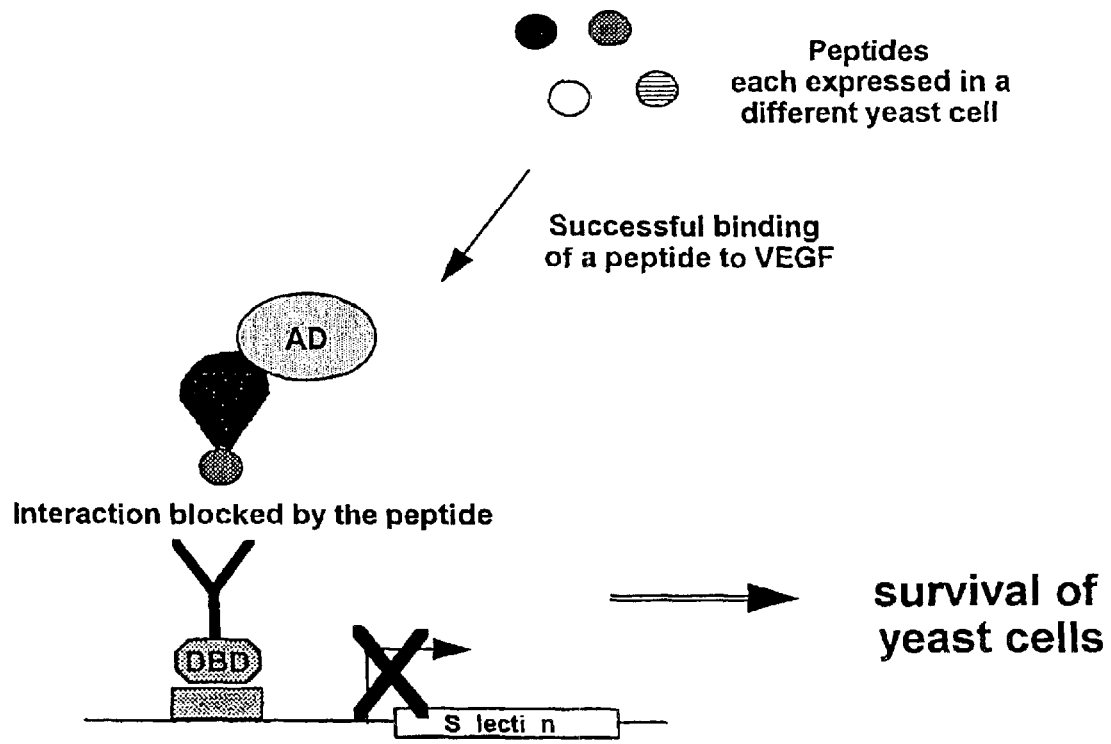
FIG. 8 represents the situation during the screening of a host cell in the presence of an antagonist.

The host cells suitable for such antagonist search are produced by transforming the host cell with sequences for at least two, and preferably two, hybrids, one such sequence encoding a first protein connected to a DNA-binding unit (in the case of polymerase II (pol II) activation a DNA-binding domain) under the control of an active promoter, and a second sequence encoding a second protein linked to an activation unit (in the case of pol II activation an activation domain), said sequence also being under the control of an active promoter. The procedure is now further described in terms of pol II activation. The DNA-binding domain is suitable to bind to a transcription activating system activating a selector/reporter gene. The transcription, however, is only activated if the binding domain and the activation domain interact. Such interaction, however, is only obtained if the two proteins connected to such domains are also interacting (see FIG. 7). The reporter gene suitable for such selection is a gene causing the death of the yeast cells upon activation, so that only such cells are able to survive, where the protein—protein interaction and thus the transcription of the protein causing the death of yeast cells is blocked (see FIG. 8).

The accordingly transformed yeast cells are then brought into contact with a DNA library as disclosed above, and those cells, producing a blocking peptide, are selected and analysed as described in more detail with regard to the p53 system.

Such a system is e.g. very suitable for the antagonist search in the case of the overexpression of specific proteins, such as e.g. the Vascular Endothelial Growth Factor (VEGF). VEGF is a secreted protein that, by interacting with its receptors present on the surface of endothelial cells forming the blood vessels, stimulates their proliferation, the formation of new blood vessels. VEGF plays a pivotal role in the growth of tumors because such growth requires the formation of new blood vessels to gain the necessary nutrients (see FIGS. 5 and 6). Thus, blocking the function of VEGF in tumors would stop blood vessel proliferation, which would lead to tumor shrinking and reduced malignancy.

In yeast cells, the VEGF-receptor interaction is reproduced in a way that it leads to the activation of an artificial gene. In contrast to the selectable positive gene used in the p53 case, activation of this artificial negative gene leads to death of the yeast cell in the presence of a chemical compound. In other words, interaction between two molecules, such as VEGF and its receptor, and the consequent artificial gene activation, produces no colonies on the appropriate terrain containing the chemical compound. In these yeast cells, as described for p53, expression vectors carrying billions of different peptides are introduced. Only those cells capable of expressing the proper small peptide that can block the VEGF-receptor interaction, and, consequently, the activation of the artificial negative gene, are allowed to grow and to form colonies on terrains containing the selective and specific chemical compound. DNA sequences encoding the active small peptide, the effector peptide, are further characterised as described in the p53 case above.

Screening for agonists in view of a defective and thus not interacting protein

As already mentioned above, also peptides "healing" the absence of a desired protein—protein interaction action due to a defect in one of the interacting proteins can be screened. In this case, the host cell is transformed formed as described above for the search for antagonists with the exception that the transformation is performed with a "correct" and a "defective" sequence encoding a correct and a defective protein, one of them being linked to a DNA-binding unit, the other one being linked to an activation unit. The monitoring system in this case comprises at least one selector/reporter gene which enables the survival of the cell, if expressed. Such a selector/reporter gene can be one as described with regard to the agonist system.

Also, such cells are brought into contact with the DNA library, and only those cells are able to survive on a specific terrain, which comprise a peptide able to restore the activity of the defective protein so that an activating interaction between the two proteins is possible, said interaction leading to the expression of a survival enabling monitoring protein.

Also in such a system, the DNA of interest can be cloned and analysed as described above.

Screening for antagonists against active protein

It is also possible that, due to a defect, a protein activating the expression of an undesired gene is expressed in too large amounts, or in the wrong cell, or at the wrong time.

In this case, a system similar to the first described system for screening for an agonist can be applied, with the amendment, that a selector/reporter gene has to be used leading to cell death in the absence of a protein-peptide interaction disrupting the protein activity.

Suitable activation systems:

Suitable activation systems for screening systems involving hybrids are known (see e.g. above cited state of the art). Some of such activation systems comprise a DNA sequence activating the transcription of a protein upon contact with an activating protein (activation of pol II) or an activation complex (activation of pol III). Such activating proteins comprise two essential parts, namely a DNA binding domain and an activation domain. Such polymerase II related activation systems are described in the state of the art. In cases where such polymerase II related activation systems are unsuitable, other systems can be used, in particular systems related to polymerase III.

A polymerase III related system is described in Marsolier, Prioleau and Sentenac, *A RNA Polymerase III Based Two-hybrid System to Study RNA Polymerase II Transcriptional Regulators*, J. Mol. Biol. 268, 243–249, 1997. However, the system disclosed therein is not very reliable. An amended system has therefore been developed, which is not only suitable for the purposes of the here disclosed inventive screening system, but for all two hybrids involving applications.

Polymerase III related activation system:

The pol III activation system is a complex comprising a DNA-binding domain and an activating protein, which interacts with a sub-unit of the transcription apparatus (see Marsolier et al.).

Although the UASG-SNR6 promoter of the state of the art (see Marsolier et al.) offers the possibility to direct pol III transcription by a protein—protein interaction, the difficulty of monitoring this event remains. All experiments showing that this artificial transcription activation works have been done by northern blot analysis. In these experiments, the UASG-SNR6 promoter controlled the expression of a "maxi" SNR6 gene in which 24 additional base pairs were inserted in order to distinguish the wild type U6 RNA from the U6 maxi RNA in a northern blot. Although northern blot analysis is sensitive to detect RNA transcripts, it is an unsuitable technique to perform a genetic screen. An alternative system for selection of an activated UASG-SNR6 promoter has thus been developed as follows.

A UASG-SNR6 promoter harbouring the wild type transcribed SNR6 sequence (reporter construct) was introduced into the yeast strain yMCM616, whose chromosomal SNR6 gene had been mutated. The strain yMCM616 survives with a wild type SNR6 gene, carried by a URA3-marked plasmid (survival construct). Transformants containing either τ138-GAL DBD fusion alone or GAL4 and τ138 fused to interacting proteins became independent from the survival construct since they had the possibility to trigger SNR6 transcription from the UASG-SNR6 reporter construct. The monitoring of tranformants containing interacting proteins was performed by selecting for the loss of the URA3-marked plasmid. This selection can be done with 5-fluoroorotic acid (FOA), an uracil precursor analog, which is metabolised to a toxic compound by the URA3 product. Only cells that are allowed to lose the URA3-plasmid (survival construct) can grow on FOA. Transformants without possibility to activate the UASG-SNR6 promoter, due to the lack of interaction between the proteins fused to GAL4 DBD and to τ138, were still dependent on the SNR6 gene carried by the URA3-marked survival construct and therefore incapable to grow on FOA.

It has now been observed that, while FOA is highly selective against wild type yeast cells, overexpression of certain proteins leads to a reduced selectivity and, consequently, to URA3 positive cells capable of growing on FOA.

Thus, screening analysis of a genomic library with such a system would be most likely susceptible to artifacts. So, there was a need to generate a well controllable and highly selective screening system, based on the RNA polymerase III two-hybrid system.

Such an alternative to the FOA/URA 3 selection system, which is better suitable for a library screening, is obtained as follows. For this purpose, yeast strains which are able to grow at 30° C. but not at 37° C. were generated. This temperature sensitivity is due to a mutation in an episomally expressed SNR6 gene which is under the control of its natural promoter (ts survival construct). The wild type SNR6 allele, whose expression can rescue the temperature sensitive phenotype, is integrated into the genome, and is under the control of the artificial UASG-SNR6 promoter. As it is the case in the original pol III two-hybrid system, the expression of this SNR6 reporter gene is dependent on the interaction between the τ138 fusion protein (τ138-X) and the UASG-bound GAL4 fusion protein (Y-GAL4 DBD). In this novel and advantageous selection system, expression of the wild type SNR6 sequence allows cell growth at the non-permissive temperature of 37° C.

Monitoring systems:

Suitable selector/reporter systems leading to cell death or cell survival when activated are known (see e.g. URA 3, LYS 2, CYH 2, HIS 3, LEU 2, Kan.$^r$).

In order to enhance the security of the screening system, it is preferred, that the monitoring system comprises two selector/reporter systems, one enabling the survival on a specific terrain, and for example a second one enabling the survival on another terrain or expressing a colouring protein allowing the visual selection of cells.

Since for the generation of a suitable host cell transformation with several DNA sequences is needed, it is preferred that all selector/reporter sequences are introduced into the same vector, so that less transformation steps are needed to get a suitably transformed host cell. This has the advantage that either a host cell with fewer selection markers can be used or that more selection markers are available for other purposes. A further advantage is that e.g. two sequences encoding different monitoring proteins can be connected to the same transcription activation sequence.

The vectors used to transform the host cells are preferably such ones that lead to an incorporation in the genome of the selector/reporter sequences, whereby the target protein encoding sequences, as well as the DNA library, preferably are present in episomal form.

Effector molecules with desired biological activity can be screened in that an inventive screening system is brought into contact with a suitable selection medium selectively allowing the survival of cells with desired target protein-effector peptide interaction.

A screening system according to the present invention is produced in that the host cells are transformed with at least one monitoring gene enabling the detection of said host cell upon transcription of said at least one monitoring gene, said at least one monitoring gene being directly or indirectly under the control of a specific activation system and, at least one DNA sequence coding for at least one target molecule, said one or more target molecule(s) being selected from the group comprising RNA sequences or proteins, said one or more target molecule(s) being responsible in their natural environment for the induction of the production and/or activity of an undesired protein or the omission of the production and/or activation of a desired protein, said at least one DNA sequence coding for said at least one target molecule being under the control of an host cell specific active promoter, preferably a host cell specific promoter, and a DNA library encoding peptides, wherein the DNA is under the control of an active promoter.

In such a production process with adivated monitoring proteins more than one nucleic acid sequence encoding a monitoring protein can be introduced into the cell on the same vector and under the control of the same specific activation system. Such proceeding is preferred in view of stability of the system, the need of markers and the screening selectivity.

A further important object of the present invention is a DNA library encoding peptides, wherein the peptide encoding nucleotide sequences are under the control of a promoter active in a specific host cell, in particular in a yeast cell. Such a DNA library is preferably produced in that genomic DNA or cDNA is fragmented by digestion or, preferably, sonication and digestion, or by synthesis of random oligonucleotides, preferably single stranded oligonucleotides, in order to generate peptide encoding sequences, said peptide encoding sequences then being introduced as such, or fused to a defined protein, into expression vectors able to transform specific host cells, whereby the peptide encoding sequences are under the control of a promoter active in a specific host cell, in particular in yeast cells.

Vectors comprising double-stranded random oligonucleotides can easily be produced by generating a 3' overhang and a blunt end. Such an overhang and blunt end are readily obtained by digestion with suitable restriction enzymes.

The random single-stranded oligonucleotides carry at the 3' end a known sequence complementary to the 3' overhang. This feature allows direct ligation of the single-stranded oligonucleotide with the 3' overhang allowing the formation of the complementary strand by polymerase activity. The resulting double-stranded sequence contains a blunt end which is then ligated with the plasmid blunt end.

This method is not limited to the generation of a DNA library of the present invention, but can be applied to any cloning of random sequences.

A further object of the invention are host cells, in particular yeast cells, comprising a polymerase III activated selection system with at least one destroyed genomic sequence encoding an essential molecule, said host cells additionally comprising a temperature sensitive mutant of said destroyed sequence under the control of an active promoter, and a sequence insensitive to non-permissive conditions under the control of a specific transcriptional activator selectively activated upon interaction of two proteins. Such sequences insensitive to non-permissive conditions are e.g. wild-type sequences.

EXAMPLES

General remarks:

All sequences mentioned herein are listed in 5'→3'-direction. They are additionally listed in the SEQUENCE LISTING following the experimental part.

Example 1

Yeast expression vectors

Figure 9:
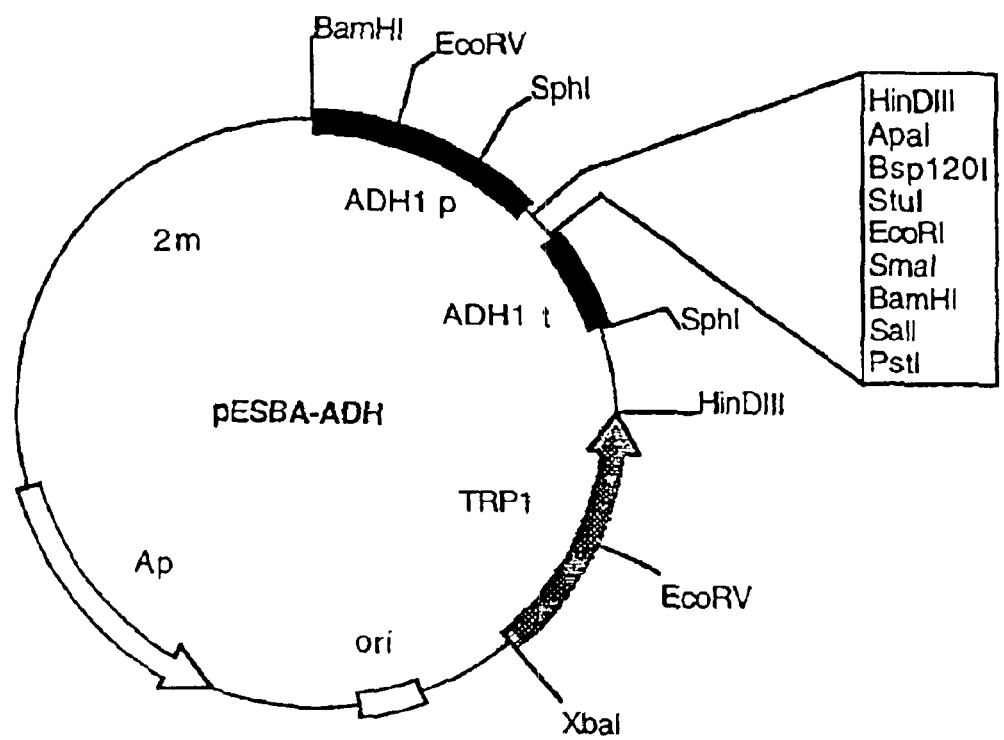
FIG. 9 shows expression vector pESBA-ADH.
Figure 10:
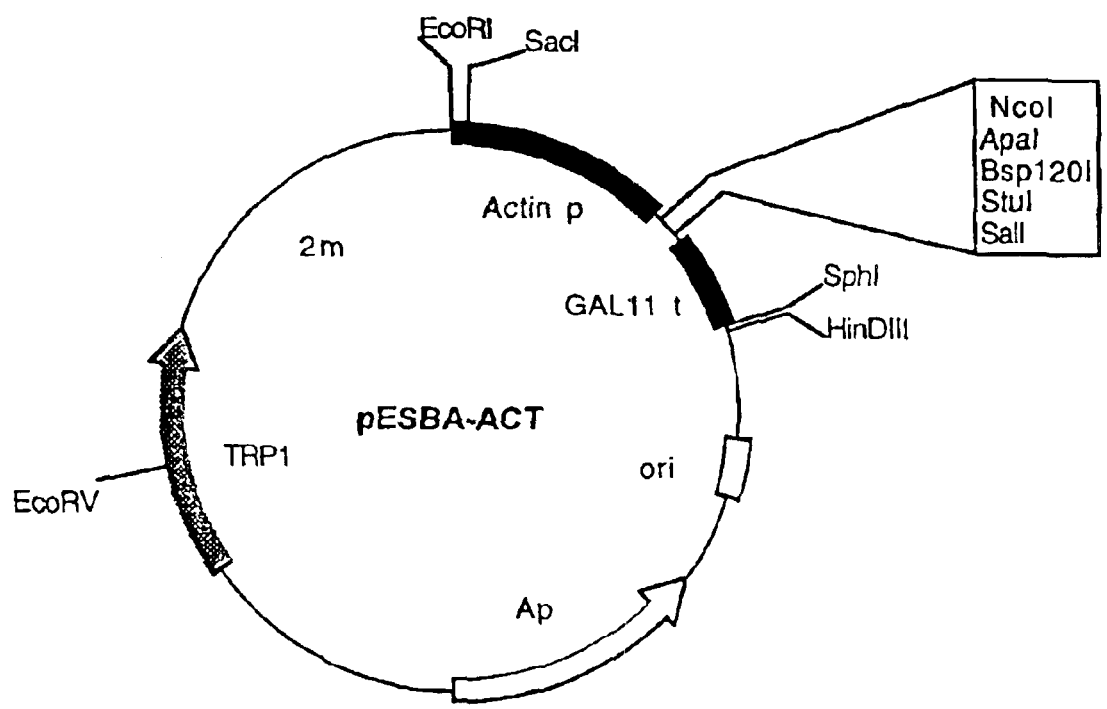
FIG. 10 shows expression vector pESBA-ACT.
Figure 11:
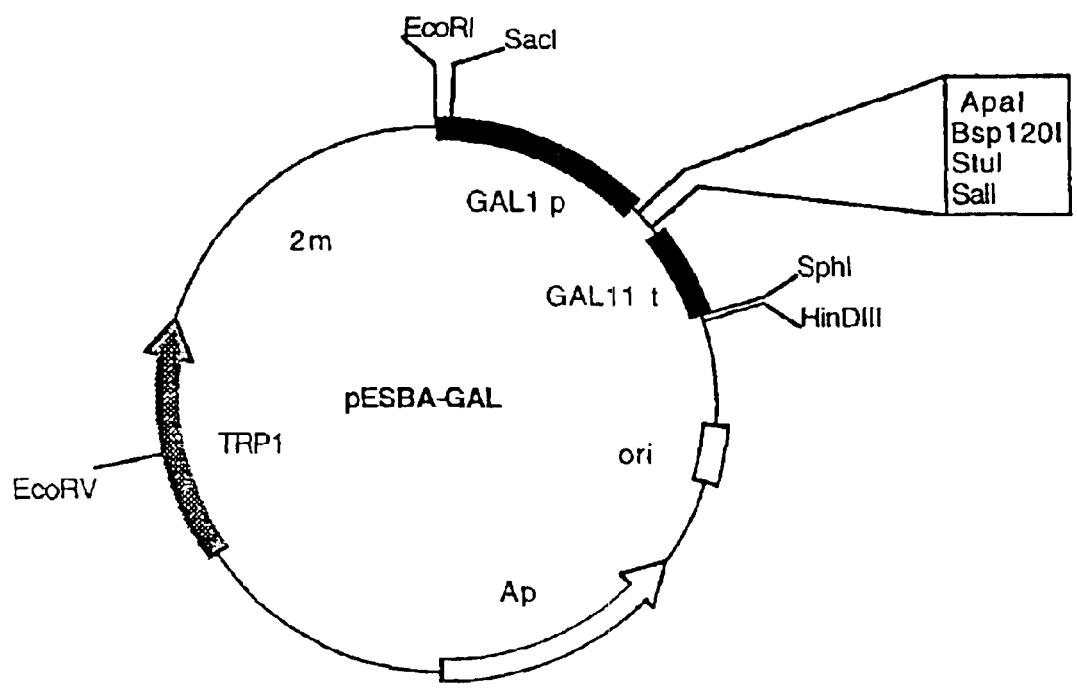
FIG. 11 shows expression vector pESBA-GAL.

DNA vectors for expression of peptides in yeast contain a selectable yeast nutritional marker, a replication origin for maintenance in yeast cells, a constitutive or inducible promoter for activation of genes encoding peptides, a transcription termination sequence, and bacterial β-lactamase gene and origin of replication for plasmid growth in E. coli. Expression vectors disclosed herein bear the standard yeast 2 μm origin of replication, the TRP1 selectable marker and one of the following yeast promoters: the constitutively expressed ADH1 and ACTIN promoters, and the inducible GAL1 promoter (FIGS. 9, 10 and 11). These expression vectors contain restriction sites immediately downstream of the translation initiation codon ATG for cloning DNA sequences encoding peptides. Translation stop codons in all three reading frames are present downstream of these cloning sites.

pESBA-ADH (FIG. 9):

This expression vector was constructed as follows: oligonucleotides AGCTTAACAAAATGGGCCCGCAGGC-CTAACTAACTAAG (SEQ. ID. No. 13) and AATTCT-TAGTTAGTTAGGCCTGCGGGCCCATTTTGTTA (SEQ. ID. No. 14) were kinased using T4 polynucleotide kinase (PNK) and annealed according to standard procedures to form a double-strand (ds) oligonucleotide. This ds oligonucleotide contains the initiation codon ATG, ApaI/Bsp120I and StuI restriction sites, stop codons TAA in all three reading frames, and cohesive ends compatible with ligation in open HindIII and EcoRI sites. The ADH1 promoter sequence was isolated from the plasmid PADNS (ref. C. Guthrie and G. R. Fink Ed., *Guide to Yeast Genetics and molecular Biology*, Academic Press, Inc. 1991) by BamHI and HindIII digestion followed by preparative electrophoresis in a 1% agarose gel. The transcription termination sequence of the ADH1 gene and part of the yeast TRP1 gene were isolated from the plasmid pGBT9 (obtained from Clontech, USA) by EcoRI and XbaI digestion followed by preparative electrophoresis in a 1% agarose gel. The expression vector backbone also carrying the remnant of the TRP1 gene was prepared by SphI and XbaI digestion followed by Calf Intestinal Phosphatase (CIP) treatment and preparative electrophoresis in a 1% agarose gel. These three DNA fragments plus the ds oligonucleotide were ligated together in one ligation step using T4 DNA ligase.

pESBA-ACT (FIG. 10):

Oligonucleotides CATGGGCCCGCAGGCCTAAC-TAACTAAG (SEQ. ID. No. 15) and TCGACTTAGTTAGT-TAGGCCTGCGGGCC (SEQ. ID. No. 16) were kinased and annealed to form ds oligonucleotides containing the initiation codon ATG, ApaI/Bsp120I and StuI restriction sites, stop codons TAA in all three reading frames, and cohesive ends compatible with ligation in open NcoI and SalI sites. This ds oligonucleotide was cloned into the expression vector pJP224 (J. Pearlberg, PhD thesis, Harvard University, Cambridge, Mass., 1995) which had been digested with NcoI and SalI restriction enzymes and treated with CIP. This vector contains the ACTIN promoter, a unique NcoI site overlapping with the initiation codon ATG, a SalI site and, immediately downstream of it, the transcription termination sequence of the GAL11 gene.

pESBA-GAL1 (FIG. 11):

The expression vector pJG4-5 (R. Brent in *Current Protocols in Molecular Biology*, Chapter 20, 1997, John Wiley & Sons, Inc.) was digested with HindIII, treated with Klenow to fill in the DNA ends, and then digested with SacI to isolate its GAL1 promoter. pESBA-ACT was digested with NcoI, treated with Klenow, and then digested with SacI to cut out the ACTIN promoter. Upon separation by electrophoresis and extraction from the agarose gel, the GAL1 promoter fragment and the pESBA-ACT backbone cured of the ACTIN promoter were ligated such as to regenerate the SacI site and join the blunt HindIII and NcoI ends.

Example 2

Yeast reporter constructs

Plasmids carrying reporter genes are designed for integration into the yeast genome. Each plasmid bears two divergently transcribed genes separated by a multiple cloning sequence (MCS). This cluster of unique restriction sites is used to insert the desired protein-binding sequences. One of the two reporter genes is LacZ, which encodes the enzyme β-galactosidase commonly used to measure gene expression in yeast (C. Kaiser et al., *Methods in Yeast Genetics, A. Cold Spring Harbor Laboratory Course Manual*, 1994 Ed.). The second gene encodes either an enzyme whose expression is required for growth of the host cell on appropriate, selective terrain, or another enzyme whose expression has to be inhibited in order to allow growth of the host cell. Reporter plasmids constructed so far contain, in addition to the LacZ coding region controlled by the GAL1 core promoter, either the selectable HIS3 gene with its own core promoter, or the URA3 coding region controlled by the SPO13 promoter (ref. M. Vidal, PNAS). Expression of the HIS3 gene is required for yeast growth on media lacking histidine. The level of HIS3 gene expression can be modulated by varying the concentration in the media of 3-aminotriazole (3-AT), a competitive inhibitor of the HIS3 gene product. In contrast, expression of the URA3 gene can be toxic to yeast cells growing on media containing the drug 5-fluorotic acid (5-FOA). In this case, cells would grow on 5-FOA-containing media only upon inhibition of URA3 expression (see *Guide to Yeast Genetics and Molecular Biology*).

pESBA-HIS3:

The Lacz reporter plasmid pJP158 (J. Pearlberg, PhD thesis, Harvard University) was digested with BglII and partially with BamHI to cut out the URA3 sequence. The fragment of 6422 base pairs containing the LacZ coding region and the GAL1 core promoter was isolated by agarose gel electrophoresis and recircularised by ligation of the compatible BglII and BamHI sites. The HIS3 coding region together with a 3' untranslated sequence of about 630 base pairs were amplified by PCR using the upstream primer GGCAGTCGACATTATATAAAGTAATGTG (SEQ. ID. No. 17) and the downstream primer GGCAGTCGACGGA-CACCAAATATGGCG (SEQ. ID. No. 18). The pJP158-derived plasmid was digested with XhoI and SalI and treated with CIP. The larger fragment was isolated by agarose gel electrophoresis. The PCR product was digested with SalI and cloned into the SalI-XhoI digested plasmid. Orientation of the insert was determined by restriction enzyme analysis, and the correct clone with the HIS3 gene transcribed in the opposite direction of the LacZ gene was amplified in bacteria.

The oligonucleotides TCGACTCTAGAGCGGCCGC-GAGCTCCCGCGGGCATGCAGATCTCCCG GGG (SEQ. ID. No. 19) and TCGACCCCGGGAGATCTGCATGC-CCGCGGGAGCTCGCGGGCCGCTCTA GAG (SEQ. ID. No. 20) were kinased and annealed to form ds oligonucleotides bearing a MCS and cohesive ends compatible with ligation into an open SalI site. These ds oligonucleotides were inserted at the unique SalI site of the plasmid described above. Sequence analysis was performed to determine the orientation of the inserted MCS and to confirm that only one SalI site was restored upon insertion of the ds oligonucleotide.

pESBA-URA3:

A sequence containing the URA3 coding region fused to the SPO13 promoter described in the paper of Vidal et al., was isolated by PCR using the upstream primer AGT-TCAGTCGACGTATCCGTTTAGCTAGTTAG (SEQ. ID. No. 21) and the downstream primer AATACTGCAG-CAGTTTTTTAGTTTTGCTGGCC (SEQ. ID. No. 22). These primers were designed such as to introduce a SalI site and a PstI site at the 5' and 3' ends of the PCR product, respectively. The HIS3 coding region and promoter present on the vector pESBA-HIS3 were cut out by SalI and PstI digestion and substituted with the SPO13-URA3 PCR product digested with SalI and PstI.

pESBA-URA3-17mer:

Oligonucleotides CGGAAGACTCTCCTCCGT (SEQ. ID. No. 23) and CTAGACGGAGGAGAGTCTTCCG-CATG (SEQ. ID. No. 24) were kinased and annealed to form ds oligonucleotides bearing two binding sites for the transcriptional activator GAL4 (17mer) and cohesive ends for ligation into open XbaI and SphI sites. pESBA-URA3 was digested with XbaI and SphI, treated with CIP, extracted with phenol, and precipitated with ethanol. The ds oligonucleotide described above was ligated into this plasmid backbone with T4 DNA ligase, and the correct sequence was confirmed by sequence analysis.

Example 3

Peptide libraries

Peptides are encoded by random DNA sequences of different length cloned into the yeast expression vectors described above. These random peptides are either expressed as such or fused to defined proteins.

Peptide expression from random synthetic oligonucleotides:

Oligonucleotides were synthesised such as to contain random nucleotide sequences of variable length (from about 15 to about 60 nucleotides) followed, at their 3' ends, by the conserved sequence GGCC. Expression vectors described above were digested with ApaI (GGGCC'C) and StuI (AGG'CCT), and subsequently purified by agarose gel electrophoresis. These linearised vectors were incubated with a 20 fold molar excess of random oligonucleotides in a 30 μl reaction mixture containing dNTP's (5 mM each), standard T4 ligase buffer, 50 mM NaCl, 1 μl T4 ligase gase and 1 μl Klenow (purchased from NEB). After incubation at 16° C. for 4 hours and at room temperature for 30 minutes, the reaction mixture was extracted with phenol and ethanol-precipitated in the presence of 2M ammonium acetate to selectively discard excess free oligonucleotides. DNA was resuspended in 10 μl water and used to transform bacteria.

Peptide expression from random genomic sequences:

Genomic DNA from various organisms such as yeast, Drosophila and mouse was isolated by standard procedure. Purified genomic DNA was sonicated such as to obtain fragments of 300–500 base pairs. After phenol extraction and ethanol precipitation, these fragments were digested with a cocktail of the restriction enzymes AciI, AluI, BfaI, NlaIII, HhaI HaeIII, RsaI, and Sau3A, and subsequently treated with T4 DNA polymerase in the presence of 100 μM of each dNTP to make all DNA ends blunt. Expression vectors described above were digested with Bsp120 I (G'GGCCC) (MBI Fermentas) and treated with Klenow to fill in the open Bsp120 I ends. The vector was then digested with StuI, extensively treated with CIP, and purified by agarose gel electrophoresis. The so prepared vectors and the blunt-end genomic DNA fragments were ligated by T4 DNA ligase according to standard protocol.

Example 4

Agonistic action to the ESBATech screening system

The agonistic action of the inventive screening system has been shown for the tumor suppressor gene p53. The tumor suppressor gene p53 is mutated in more than 50% of all human cancers which results in the inability to properly bind to the p53 binding site sin target genes responsible to induce cell cycle arrest or apoptosis. The four most commonly found mutations occur in the DNA binding domain of p53 and lead to a single amino acid substitution. For one such mutation (p53 R273H), it has been shown that a synthetic 22 amino acid long peptide (22mer peptide 46), stemming from the carboxy-terminal part of p53 (361–382) when fused to the *Drosophila Antennapedia* internalisation domain (17 amino acids), can restore DNA binding activity of the mutated p53 (Selivanova et al., *Restauration of the Growth Suppression Function* . . . , Nature Medicine, Vol. 3 No. 6, 632 ff., 1997). The present inventors now found that the 22 amino acid long peptide, when expressed from the pESBA-ADH or pESBA-ACT vector, is sufficient to partially reactivate mutated p53 R273H in transactivation experiments. This opens the possibility to use the peptide libraries according to the present invention to screen for peptides which restore the mutated p53 to wild type activity or to use this system to screen for agonistic actions of peptides in general.

Cloning of wild type and mutated p53

Wild type p53 has been cloned by PCR into the HindIII restriction sites of the yeast expression vector pGAD424 obtained by Clontec, using the following primers; upstream GCACAAGCTTACCATGGAGGAGCCGCAGCTAG (SEQ. ID. No. 1); downstream GCGT-CAAGCTTTCAGTCTGAGTCAGGCC (SEQ. ID. No. 2). Amino acid changes were introduced in p53, covering the four most commonly found mutations in cancer cells (Hollstein et al., Science 253, 49, 1991). These mutations had been introduced by PCR using degenerated primers:

```
R175H: upstream

GGAGGTTGTGAGGCACTGCCCCCACC (SEQ. ID. No. 3); downstream

GGTGGGGGCAGTGCCTCACAACCTCC (SEQ. ID. No. 4)

R248W, R249P: upstream

GGGCGGCATGAACTGGCCACCCATCCTCACCATCATCAC (SEQ. ID. No. 5); downstream

GTGATGATGGTGAGGATGGGTGGCCAGTTCATGCCGCC (SEQ. ID. No. 6)

R273H: upstream

GGAACAGCTTTGAGGTGCACGTTTGTGCCTGTCC (SEQ. ID. No. 7); downstream

GGACAGGCACAAACGTGCACCTCAAAGCTGTTCC (SEQ. ID. No. 8)
```

-continued

R282W: upstream

CCTGGGAGAGACTGGCGCACAGAGG (SEQ. ID. No. 9); downstream

CCTCTGTGCGCCAGTCTCTCCCAGG (SEQ. ID. No. 10)

Cloning of p53 binding sites

Figure 12:
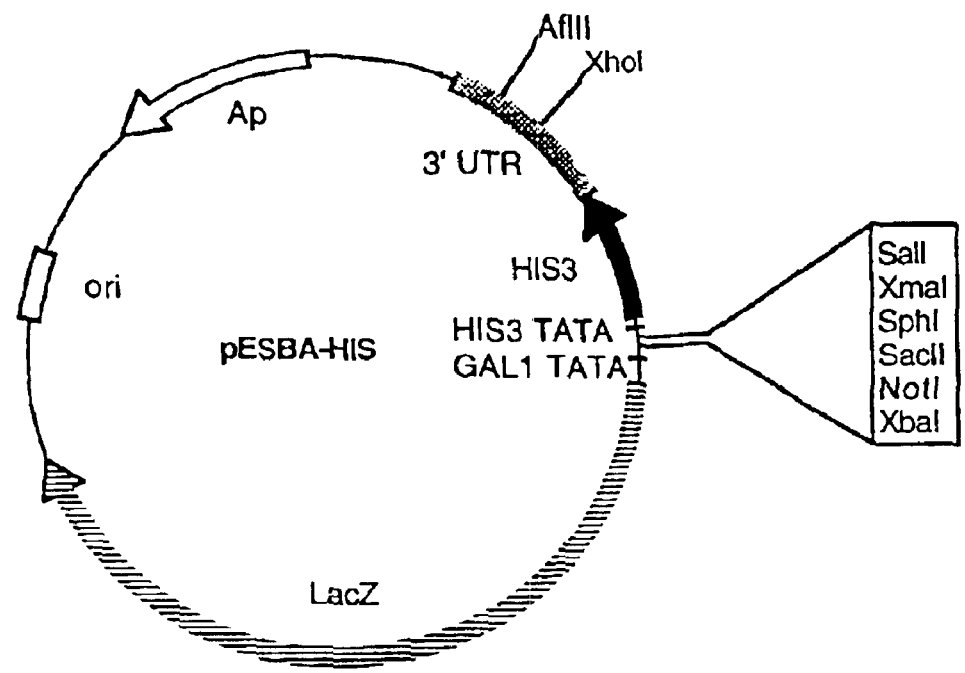
FIG. 12 shows reporter vector pESBA-HIS.
Figure 13:
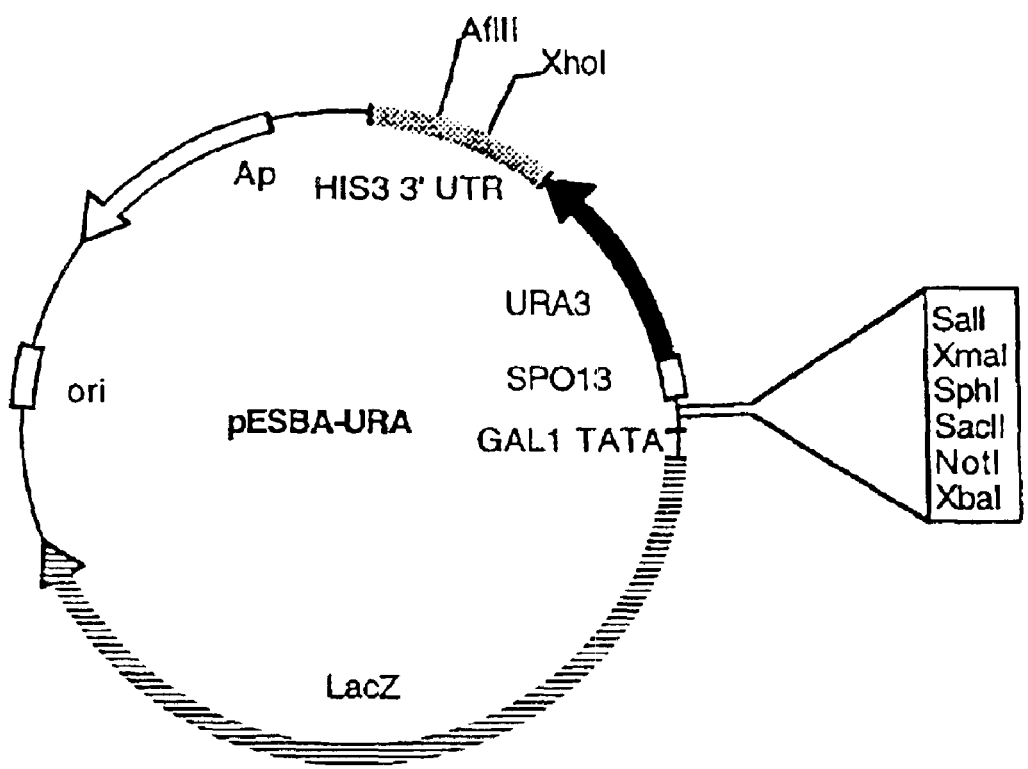
FIG. 13 shows reporter vector pESBA-URA.
Figure 14:
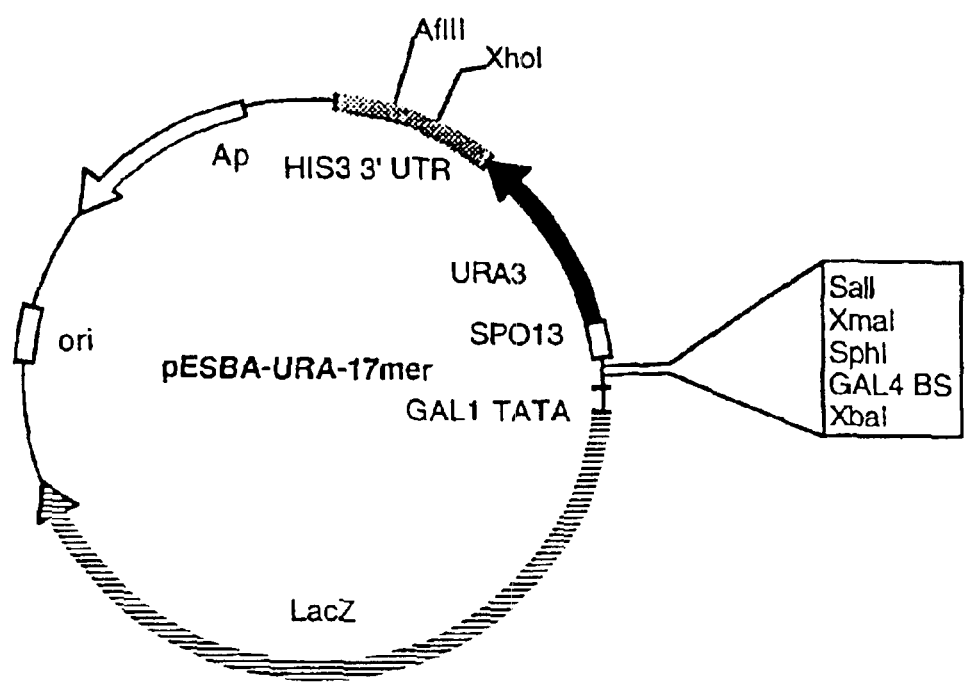
FIG. 14 shows reporter vector pESBA-URA-17mer.

The four putative p53 binding sites were cloned (Bian and Sun, Proc. Natl. Acad. Sci. USA 94, 14753, 1997; El-Deiry et al., Cell 75, 817, 1993; Kern et al., Science 256, 827, 1992) into the XmaI-SphI site of pESBA-HIS (FIG. 12) using double stranded oligonucleotides with the corresponding restriction enzyme overhangs resulting in pDE4xp53BS. The sequence of the oligonucleotides is as follows: upstream CCGGGACTTGCCTGGAAACATGTCCAGTAGACATG-TTCTTAGGGCTTGCTTGCATG( SEQ. ID. No. 11); downstream CAAGCAAGCCCTAAGAACATGTCTAC-TGGACATGTTTCCAGGCAAGTC(SEQ. ID. No. 12)

The reporter vector pDE4xp53BS was linearised at the HIS3 3'UTR using XhoI and introduced into the yeast strain JPY9 (J. Pearlberg, Ph.D. thesis, Harvard University; A. Barberis et al., Contact with a Component of the . . . , Cell. Vol. 81, 359–368, 1995), resulting in YDE4xp53.

Expression and transactivation of wild type and mutated p53

Yeast strain YDE4xp53 was transformed with the conventional lithium acetate method (Methods in Yeast Genetics, a Cold Spring Harbor Laboratory Course Manual, Cold Spring Harbor Laboratory Press, 1994) with wild type and mutated p53 expression vectors. Transactivation potential of the different p53 molecules was determined by measurement of the LacZ expression on X-gal plates and liquid beta-galactosidase assays as described (Escher and Schaffner, Gene Activation at a Distance and Telomeric Silencing . . . , Mol. Gen. Genet. (1997) 256; 456–461). The expression level of wild type and mutated p53 was imonitored by Western blot using PAb421 monoclonal antibody (Hupp and Lane, Curr. Biol. 4, 865, 1994). Wild type and mutated p53 showed same intracellular protein level.

Example 5

Testing the antagonistic action of peptides in yeast

To test the antagonistic action of short protein fragments or peptides in yeast, it was checked whether high production of a peptide could inhibit a defined molecular interaction. For this purpose, the interaction between GAL4, a yeast DNA-binding transcriptional activator, and GAL11P, a component of the RNA polymerase II holoenzyme, which has been shown to activate transcription (A. Barberis et al., *Contact with a Component of the Polymerase II Holoenzyme Suffices for Gene Activation*, Cell. Vol. 81, 359–368, 1995; S. Farrell et al., *Gene activation by recruitment of the RNA polymerase II holoenzyme*, Genes & Development 10, 2359–2367, 1996) was exploited. This protein—protein interaction and its effect on gene expression could be specifically inhibited by expressing a short protein fragment from a high-copy plasmid (2 $\mu$m) in yeast.

The yeast strain used in these experiments is a derivative of JPY9 (MATα, ura3-52, his3Δ200, leu2Δ1, trp1Δ63, lys2Δ385, gal4Δ11) (A. Barberis et al., Cell, Vol. 81, 359–368) in which the reporter construct pESBA-17mer-URA3 was integrated at the his3 locus. Integration through homologous recombination was piloted by linearisation of the reporter plasmid at the XhoI site prior to yeast transformation. Expression of the URA3 gene was exploited to select for stable integrants on ura-media. Since basal level expression of the SPO13-URA3 fusion gene is too low to allow cell growth on ura-media, yeast were co-transformed with a plasmid vector expressing GAL4 which, by binding the 17mer sequence, activated URA3 expression. Upon selection for integration of the reporter construct, this plasmid was readily cured from yeast cells by negative selection for URA3 expression on media containing 5-FOA (ref. *Guide to Yeast Genetics and Molecular Biology*)

Activation of the divergent LacZ and URA3 reporter genes in the yeast strain described above was induced by co-expression of the DNA-binding domain of GAL4 (amino acid residues 1–100) and GAL11P. GAL4(1–100) was expressed from the plasmid pRJR217 (Y. Wu et al., *Quantification of Putative Activator- Target Affinities* . . . , EMBO J. 15, 3951–3963, 1996), while GAL11P was expressed from pSO$_{28}$ (A. Barberis et. al., Cell Vol. 81, 359–368). As expected, GAL4(1–100) did not activate transcription in the absence of GAL11P. To inhibit the GAL4(1–100)-GAL11P interaction and, as a consequence of this, activation of the reporter genes, a peptide comprising the GAL4 residues 58–97, which are known to contain the GAL11P-interacting sequence, was overexpressed. This peptide was overexpressed from the vector PESBA-ADH1. Inhibition of reporter gene expression was monitored by measurement of β-galactosidase activity in a standard ONPG assay, and by cell growth on media containing 5-FOA (*Methods in Yeast Genetics, A. Cold Spring Harbor Laboratory Course Manual,* 1994 Edition).

While there are shown and described presently preferred embodiments of the invention, it is to be distinctly understood that the invention is not limited thereto but may be otherwise variously embodied and practised within the scope of the following claims.

What is claimed is:

1. A screening system for peptide agonists comprising a eukaryotic host cell stably transformed with a selection system and an effector peptide expressing system, said selection system enabling the survival of the cells in the case of a desired interaction between at least one defective target molecule and an effector peptide with agonist activity, said desired interaction restoring the normal function of said defective are molecule whereby said selection system comprises
(a) at least one monitoring gene enabling the detection of said host cell upon transcription of said monitoring gene, said at least one monitoring gene being directly or indirectly under the control of a specific activation system and,
(b) at least one DNA sequence coding for at least one defective target molecule, said at least one defective target molecule being selected from the group consisting of RNA sequences and proteins, said at least one defective target molecule being responsible in its natural environment for the induction of the production and/or the activity of an undesired protein or the omission of the production and/or the activation of a desired protein, said at least one DNA sequence coding for said at least one defective target molecule being under the control of an host cell specific active promoter, preferably a host cell specific promoter, whereby said specific activation system is selectively modulated in the presence of at least one specific interaction between said at least one defective target molecule and an effector peptide with agonist activity, whereby said specific activation system upon modulation directly or indirectly modulates the transcription of at least one monitoring gene enabling the survival of said host cell, and whereby said effector peptide expressing system comprises a peptide encoding nucleic acid sequence under the control of a host cell active promoter.

2. The screening system according to claim 1, wherein at least one of said monitoring genes is a nucleic acid sequence encoding at least one monitoring protein enabling the detection of said host cell upon expression of said at least one monitoring protein, said at least one nucleic acid encoding said at least one monitoring protein being under the control of said specific activation system, and whereby said specific activation system upon modulation modulates the expression of at least one monitoring protein enabling the survival of said host cell.

3. The screening system of claim 1, wherein the eukaryotic host cell is a yeast cell.

4. The screening system of claim 1, wherein said at least one DNA sequence coding for said at least one defective target molecule encodes a protein that is partially or completely inactive in its natural environment.

5. The screening system of claim 1, wherein said at least one DNA sequence coding for said at least one defective target molecule encodes at least two target molecules that upon interaction induce an undesired response in their natural environment.

6. The screening system of claim 1, wherein said at least one DNA sequence coding for said at least one defective target molecule encodes a protein inducing an undesired response in its natural environment.

7. The screening system of claim 1, wherein said at least one DNA sequence coding for said at least one defective target molecule encodes at least two target molecules, whereby at least one of said molecules has a defect making a desired interaction with at least one further target molecule impossible.

8. The screening system of claim 1, wherein the selection system comprises a first nucleic acid sequence encoding a first monitoring protein and a second nucleic acid sequence encoding a second monitoring protein, wherein the first nucleic acid sequence is a selector/reporter gene, which upon activation or inactivation in a selection medium, enables cell survival, and the second nucleic acid sequence is a reporter gene, which upon activation, expresses the second monitoring protein, which is a coloring protein, said first and second nucleic acid sequences being under the control of the same specific activation system.

9. The screening system of claim 1, wherein said effector peptide expressing system encodes modifications of a specific peptide.

10. A process for the screening of effector molecules with desired biological activity, wherein a screening system according to claim 1 is brought into contact with a selection medium selectively allowing the survival of cells with desired target molecule-effector peptide interaction.

11. A process for the production of a screening system according to claim 1, comprising transforming host cells with (a) at least one monitoring gene enabling the detection of said host cell upon transcription of said at least one monitoring gene, said at least one monitoring gene being directly or indirectly under the control of a specific activation system and, (b) at least one DNA sequence coding for at least one defective target molecule, said at least one defective target molecule being selected from the group consisting of RNA sequences and proteins, said at least one defective target molecule being responsible in its natural environment for the induction of the production and/or activity of an undesired protein or the omission of the production and/or activation of a desired protein, said at least one DNA sequence coding for said at least one defective target molecule being under the control of a host cell specific active promoter, and (c) a DNA library encoding peptides, wherein the peptide encoding regions of the DNA library are under the control of an active promoter.

12. The process of claim 11, wherein more than one nucleic acid sequence encoding a monitoring system is introduced into the cell on the same vector and under the control of the same specific activation system.

13. The screening system of claim 1, wherein said at least one DNA sequence coding for said at least one defective target molecule is under control of a host cell specific promoter.

14. The screening system of claim 1, wherein said effector peptide expressing system comprises a peptide encoding nucleic acid sequence which is under control of a host cell specific promoter.

* * * * *

UNITED STATES PATENT AND TRADEMARK OFFICE
CERTIFICATE OF CORRECTION

PATENT NO. : 6,821,728 B1 Page 1 of 1
DATED : November 23, 2004
INVENTOR(S) : Dominik Escher et al.

It is certified that error appears in the above-identified patent and that said Letters Patent is hereby corrected as shown below:

Title page,
Item [73], Assignee, after "ESBATech AG, Zurich (CH) please insert -- Universität Zurich, Zurich (CH) --

Column 25,
Line 55, please delete "defective are molecule" and insert -- defective target molecule, -- in its place.

Column 26,
Line 51, after "being under the control of" please delete "an host cell" and insert -- a host cell -- in its place.

Signed and Sealed this

First Day of March, 2005

JON W. DUDAS
*Director of the United States Patent and Trademark Office*

SEQUENCE LISTING

<160> NUMBER OF SEQ ID NOS: 24

<210> SEQ ID NO 1
<211> LENGTH: 32

-continued

```
<212> TYPE: DNA
<213> ORGANISM: Artificial sequence
<220> FEATURE:
<223> OTHER INFORMATION: Upstream Primer

<400> SEQUENCE: 1
gcacaagctt accatggagg agccgcagct ag                                     32

<210> SEQ ID NO 2
<211> LENGTH: 28
<212> TYPE: DNA
<213> ORGANISM: Artificial sequence
<220> FEATURE:
<223> OTHER INFORMATION: Downstream Primer

<400> SEQUENCE: 2
gcgtcaagct ttcagtctga gtcaggcc                                          28

<210> SEQ ID NO 3
<211> LENGTH: 26
<212> TYPE: DNA
<213> ORGANISM: Artificial sequence
<220> FEATURE:
<223> OTHER INFORMATION: Upstream Primer

<400> SEQUENCE: 3
ggaggttgtg aggcactgcc cccacc                                            26

<210> SEQ ID NO 4
<211> LENGTH: 26
<212> TYPE: DNA
<213> ORGANISM: Artificial sequence
<220> FEATURE:
<223> OTHER INFORMATION: Downstream Primer

<400> SEQUENCE: 4
ggtgggggca gtgcctcaca acctcc                                            26

<210> SEQ ID NO 5
<211> LENGTH: 39
<212> TYPE: DNA
<213> ORGANISM: Artificial sequence
<220> FEATURE:
<223> OTHER INFORMATION: Upstream Primer

<400> SEQUENCE: 5
gggcggcatg aactggccac ccatcctcac catcatcac                              39

<210> SEQ ID NO 6
<211> LENGTH: 39
<212> TYPE: DNA
<213> ORGANISM: Artificial sequence
<220> FEATURE:
<223> OTHER INFORMATION: Downstream Primer

<400> SEQUENCE: 6
gtgatgatgg tgaggatggg tggccagttc atgccgccc                              39

<210> SEQ ID NO 7
<211> LENGTH: 34
<212> TYPE: DNA
<213> ORGANISM: Artificial sequence
<220> FEATURE:
<223> OTHER INFORMATION: Upstream Primer
```

-continued

```
<400> SEQUENCE: 7
ggaacagctt tgaggtgcac gtttgtgcct gtcc                          34

<210> SEQ ID NO 8
<211> LENGTH: 34
<212> TYPE: DNA
<213> ORGANISM: Artificial sequence
<220> FEATURE:
<223> OTHER INFORMATION: Downstream Primer

<400> SEQUENCE: 8
ggacaggcac aaacgtgcac ctcaaagctg ttcc                          34

<210> SEQ ID NO 9
<211> LENGTH: 25
<212> TYPE: DNA
<213> ORGANISM: Artificial sequence
<220> FEATURE:
<223> OTHER INFORMATION: Upstream Primer

<400> SEQUENCE: 9
cctgggagag actggcgcac agagg                                    25

<210> SEQ ID NO 10
<211> LENGTH: 25
<212> TYPE: DNA
<213> ORGANISM: Artificial sequence
<220> FEATURE:
<223> OTHER INFORMATION: Downstream Primer

<400> SEQUENCE: 10
cctctgtgcg ccagtctctc ccagg                                    25

<210> SEQ ID NO 11
<211> LENGTH: 56
<212> TYPE: DNA
<213> ORGANISM: Artificial sequence
<220> FEATURE:
<223> OTHER INFORMATION: Oligonucleotide

<400> SEQUENCE: 11
ccgggacttg cctggaaaca tgtccagtag acatgttctt agggcttgct tgcatg  56

<210> SEQ ID NO 12
<211> LENGTH: 48
<212> TYPE: DNA
<213> ORGANISM: Artificial sequence
<220> FEATURE:
<223> OTHER INFORMATION: Oligonucleotide

<400> SEQUENCE: 12
caagcaagcc ctaagaacat gtctactgga catgtttcca ggcaagtc           48

<210> SEQ ID NO 13
<211> LENGTH: 38
<212> TYPE: DNA
<213> ORGANISM: Artificial sequence
<220> FEATURE:
<223> OTHER INFORMATION: Oligonucleotide

<400> SEQUENCE: 13
agcttaacaa aatgggcccg caggcctaac taactaag                      38
```

```
<210> SEQ ID NO 14
<211> LENGTH: 38
<212> TYPE: DNA
<213> ORGANISM: Artificial sequence
<220> FEATURE:
<223> OTHER INFORMATION: Oligonucleotide

<400> SEQUENCE: 14
aattcttagt tagttaggcc tgcgggccca ttttgtta                          38

<210> SEQ ID NO 15
<211> LENGTH: 28
<212> TYPE: DNA
<213> ORGANISM: Artificial sequence
<220> FEATURE:
<223> OTHER INFORMATION: Oligonucleotide

<400> SEQUENCE: 15
catgggcccg caggcctaac taactaag                                     28

<210> SEQ ID NO 16
<211> LENGTH: 28
<212> TYPE: DNA
<213> ORGANISM: Artificial sequence
<220> FEATURE:
<223> OTHER INFORMATION: Oligonucleotide

<400> SEQUENCE: 16
tcgacttagt tagttaggcc tgcgggcc                                     28

<210> SEQ ID NO 17
<211> LENGTH: 28
<212> TYPE: DNA
<213> ORGANISM: Artificial sequence
<220> FEATURE:
<223> OTHER INFORMATION: Upstream Primer

<400> SEQUENCE: 17
ggcagtcgac attatataaa gtaatgtg                                     28

<210> SEQ ID NO 18
<211> LENGTH: 27
<212> TYPE: DNA
<213> ORGANISM: Artificial sequence
<220> FEATURE:
<223> OTHER INFORMATION: Downstream Primer

<400> SEQUENCE: 18
ggcagtcgac ggacaccaaa tatggcg                                      27

<210> SEQ ID NO 19
<211> LENGTH: 50
<212> TYPE: DNA
<213> ORGANISM: Artificial sequence
<220> FEATURE:
<223> OTHER INFORMATION: Oligonucleotide

<400> SEQUENCE: 19
tcgactctag agcggccgcg agctcccgcg ggcatgcaga tctcccgggg             50

<210> SEQ ID NO 20
<211> LENGTH: 51
<212> TYPE: DNA
<213> ORGANISM: Artificial sequence
<220> FEATURE:
<223> OTHER INFORMATION: Oligonucleotide
```

```
-continued

<400> SEQUENCE: 20 tcgacccegg gagatctgca tgcccgcggg agctcgcggg ccgctctaga g         51

<210> SEQ ID NO 21
<211> LENGTH: 32
<212> TYPE: DNA
<213> ORGANISM: Artificial sequence
<220> FEATURE:
<223> OTHER INFORMATION: Upstream Primer

<400> SEQUENCE: 21
agttcagtcg acgtatccgt ttagctagtt ag                              32

<210> SEQ ID NO 22
<211> LENGTH: 32
<212> TYPE: DNA
<213> ORGANISM: Artificial sequence
<220> FEATURE:
<223> OTHER INFORMATION: Downstream Primer

<400> SEQUENCE: 22
aatactgcag cagtttttta gttttgctgg cc                              32

<210> SEQ ID NO 23
<211> LENGTH: 18
<212> TYPE: DNA
<213> ORGANISM: Artificial sequence
<220> FEATURE:
<223> OTHER INFORMATION: Oligonucleotide

<400> SEQUENCE: 23
cggaagactc tcctccgt                                              18

<210> SEQ ID NO 24
<211> LENGTH: 26
<212> TYPE: DNA
<213> ORGANISM: Artificial sequence
<220> FEATURE:
<223> OTHER INFORMATION: Oligonucleotide

<400> SEQUENCE: 24
ctagacggag gagagtcttc cgcatg                                     26
```